(12) United States Patent
Papini et al.

(10) Patent No.: US 10,660,566 B2
(45) Date of Patent: May 26, 2020

(54) CARDIO-RESPIRATORY FITNESS ASSESSMENT

(71) Applicant: KONINKLIJKE PHILIPS N.V., Eindhoven (NL)

(72) Inventors: Gabriele Papini, Eindhoven (NL); Francesco Sartor, Eindhoven (NL); Alberto Giovanni Bonomi, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 447 days.

(21) Appl. No.: 15/526,553

(22) PCT Filed: Nov. 11, 2015

(86) PCT No.: PCT/IB2015/058712
§ 371 (c)(1),
(2) Date: May 12, 2017

(87) PCT Pub. No.: WO2016/075635
PCT Pub. Date: May 19, 2016

(65) Prior Publication Data
US 2017/0311883 A1 Nov. 2, 2017

Related U.S. Application Data

(60) Provisional application No. 62/093,661, filed on Dec. 18, 2014, provisional application No. 62/079,849, filed on Nov. 14, 2014.

(51) Int. Cl.
*A61B 5/00* (2006.01)
*G06F 19/00* (2018.01)
*A61B 5/11* (2006.01)

(52) U.S. Cl.
CPC .............. *A61B 5/4884* (2013.01); *A61B 5/11* (2013.01); *A61B 5/1123* (2013.01); *A61B 5/486* (2013.01);
(Continued)

(58) Field of Classification Search
USPC ........................................................ 600/535
See application file for complete search history.

(56) References Cited

U.S. PATENT DOCUMENTS

2001/0039503 A1 * 11/2001 Chan .................... G06F 19/325
 705/2
2008/0161653 A1 7/2008 Lin
(Continued)

FOREIGN PATENT DOCUMENTS

EP 1338241 A1 * 8/2003 ......... A61B 5/02438
EP 1338241 A1 8/2003
(Continued)

OTHER PUBLICATIONS

Bassett D.R. Jr., et al., "Limiting Factors for Maximum Oxygen Uptake and Determinants of Endurance Performance", Medicine & Science in Sports & Exercise Jan. 2000;32(1):70-84.
(Continued)

*Primary Examiner* — Christian Jang
*Assistant Examiner* — Mitchell E Alter (57) ABSTRACT

Methods and systems for assessing cardio-respiratory fitness (CRF) with the use of body motion data is disclosed. Specific measurements of body movement (for example, motion amplitude or velocity, or distance covered during repetitive displacement) are dependent on a user's fitness level. Embodiments prompt the user to execute a simple set of periodic movements which can be used to estimate cardiovascular function (e.g., $VO_2^{max}$). Body motion data, such as activity count, accelerometer signals, or cadence of
(Continued)

motion, is captured and analyzed to estimate the user's fitness. The combination of body motion data with various physical measurements (e.g. body weight, height, BMI) permits the method to predict the user's $VO_2^{max}$ or similar physical fitness parameters.

22 Claims, 5 Drawing Sheets

(52) U.S. Cl.
CPC .......... *A61B 5/4866* (2013.01); *A61B 5/4872* (2013.01); *A61B 5/7267* (2013.01); *A61B 5/742* (2013.01); *G06F 19/3481* (2013.01)

(56) References Cited

U.S. PATENT DOCUMENTS

| | | | |
|---|---|---|---|
| 2012/0232360 A1* | 9/2012 | Maueler | A61B 5/0205 600/301 |
| 2014/0163343 A1 | 6/2014 | Heneghan | |
| 2014/0180033 A1 | 6/2014 | Altini | |
| 2014/0249429 A1 | 9/2014 | Tran | |
| 2014/0288438 A1 | 9/2014 | Venketraman | |
| 2015/0320362 A1 | 11/2015 | Hasegawa et al. | |

FOREIGN PATENT DOCUMENTS

| | | |
|---|---|---|
| GB | 2422790 A | 8/2006 |
| JP | 2003175139 A | 6/2003 |
| JP | 2004073272 A | 3/2004 |

OTHER PUBLICATIONS

Arena R. et al., "Assessment of Functional Capacity in Clinical and Research Settings: A Scientific Statement from the American Heart Association Committee on Exercise, Rehabilitation, and Prevention of the Council on Clinical Cardiology and the Council on Cardiovascular Nursing", Circulation—Journal of the American Heart Association, Jul. 17, 2007;116(3):329-43.

Greenland P. et al., "2010 ACCF/AHA Guideline for Assessment of Cardiovascular Risk in Asymptomatic Adults: A Report of the American College of Cardiology Foundation/American Heart Association Task Force on Practice Guidelines", Journal of teh American College of Cardiology, Dec. 14, 2010;56(25):e50-103.

Kline G.M. et al., "Estimation of VO2max from a One-Mile Track Walk, Gender, Age, and Body Weight", Medicine & Science in Sports & Exercise, Jun. 1987;19(3):253-9.).

Medical Devices & Equipment—IHS Technology http://www.imsresearch.com/press-release/sports_and_fitness_app_market_to_expand_by_more_than_60_percent_in_five_years&from=all_pr Webpage Downloaded May 9, 2017.

* cited by examiner

CARDIO-RESPIRATORY FITNESS ASSESSMENT

CROSS-REFERENCE TO RELATED APPLICATIONS

The present application claims the benefit under 35 U.S.C. § 371 of International Application No. PCT/IB2015/058712, filed on Nov. 11, 2015, which claims the benefit of and priority to U.S. provisional application No. 62/079,849, filed on Nov. 14, 2014, and priority to United States provisional application no. 62/093,661, filed on Dec. 18, 2014, the entire disclosure of which is incorporated by reference as if set forth in its entirety herein.

TECHNICAL FIELD

The present invention relates to methods and apparatus for the assessment of cardio-respiratory fitness, and in particular to methods and apparatus for the indirect estimation of cardio-respiratory fitness.

BACKGROUND

Assessment of cardio-respiratory fitness (CRF) is important in several fields, such as for the sports and fitness industry, for clinical diagnostic procedures, for prognostic and rehabilitation procedures, and for self-monitoring in asymptomatic individuals. The direct measurement of CRF requires maximal physiological effort, which is associated with a greater risk of cardiovascular events, and requires expensive devices and trained personnel. The indirect estimation of fitness overcomes some of these limitations but still requires the patient to undergo a rigorous specific protocol. Indirect estimation requires time and often involves the use of specific equipment (such as lab bicycles, steps, etc.).

Cardiovascular function is ascribable to maximal cardiac output, which, via Fick's principle, is related to maximal oxygen uptake ($VO_2^{max}$). In athletes, $VO_2^{max}$ provides valuable information about their aerobic power. Aerobic power is a fundamental determinant of endurance sport performance and an indicator of training efficacy. In the clinical setting, $VO_2^{max}$ provides key diagnostic and prognostic information in several clinical populations, such as patients with coronary artery disease or heart failure. Likewise, cardiovascular function assessment can be important to evaluate fitness in asymptomatic adults.

Although direct determination of $VO_2^{max}$ is the most accurate method, it requires a maximal level of exertion by the subject. This results in a higher risk of adverse events in individuals with intermediate to high risk of cardiovascular problems. Moreover, a respiratory gas analysis system is needed, which requires operator expertise and involves additional costs.

Estimation of $VO_2^{max}$ during sub-maximal exercise testing can offer an effective alternative. Over the past decades many protocols have been developed for this purpose. However, sub-maximal protocols require that the user follows a standardized exercise protocol. In many cases these exercise protocols require time (3 to 6 minutes) and small pieces of equipment (steps, treadmill, ergometers, etc.). Moreover, the exercise protocol has to be followed rigorously and usually requires the presence of trained personnel—such as a doctor, a researcher, or a personal trainer—in order to allow an accurate estimation of $VO_2^{max}$. Because of these requirements, $VO_2^{max}$ cannot be calculated easily, anytime and everywhere.

Accordingly, there is a need for methods and apparatus to determine $VO_2^{max}$ and other cardio-respiratory fitness parameters.

SUMMARY

This summary is provided to introduce a selection of concepts in a simplified form that are further described below in the Detailed Description section. This summary is not intended to identify key features or essential features of the claimed subject matter, nor is it intended to be used as an aid in determining the scope of the claimed subject matter.

Embodiments of the present invention relate to methods and apparatus for the indirect determination of cardio-respiratory fitness parameters such as $VO_2^{max}$. These embodiments derive from the observation that specific features of body movement (e.g., motion amplitude, movement velocity, distance covered during repetitive displacement, etc.) are dependent on the fitness level of the user. For example, a patient with high flexibility and muscle strength, which are elements correlated to cardio-respiratory fitness, would perform movements in a quicker and more repetitive way than a less fit subject.

Accordingly, a simple set of periodic body movements involving a significant portion of the body's musculature (such as squatting up and down) can be used to estimate $VO_2^{max}$ and other cardio-respiratory fitness parameters. Embodiments of the present invention use body motion data, such as activity count, accelerometer signals, cadence of motion, etc., to estimate, e.g., $VO_2^{max}$, and a system providing feedback such as sound signals to guide the user during the execution of the periodic body movements.

These exercises can be done by almost everyone nearly anytime and almost everywhere without skilled supervision. The user can do these exercises whenever he wants so that he can avoid times when his heart rate is altered by stress, fatigue, caffeine, etc. There is no need for expensive devices, simply a motion sensor (e.g., an accelerometer).

In one aspect, embodiments of the present invention relate to a method for determining at least one physical fitness parameter of a user with a computing unit. The method includes receiving physical characteristics data concerning the user at the computing unit, providing a stimulus to prompt the user to perform an exercise protocol, receiving data describing the motion of the user's body during the performance of the exercise protocol at the computing unit, and computing at least one physical fitness parameter utilizing said body motion data and said physical characteristics data.

In one embodiment, the at least one physical fitness parameter is selected from the group consisting of maximal oxygen uptake and body composition. In one embodiment, the method further includes displaying the computed physical fitness parameter to a user. In one embodiment, the exercise protocol comprises periodic body movements involving a significant number of the user's body muscles. In one embodiment, the body motion data are selected from the group consisting of the amplitude of the motion of the user's body, the speed of the motion of the user's body, the number of repetitions of the motion of the user's body, and the relation between motion features during different parts of the protocol exercise.

In one embodiment, the physical characteristics data are selected from the group consisting of the user's body weight, the user's body height, the user's body fat percentage, the user's age, and the user's body mass index. In one embodiment, computing at least one physical fitness parameter includes a waveform analysis of the body motion data. In another embodiment, computing at least one physical fitness parameter includes at least one of a regression analysis and a statistical learning analysis of the body motion data. In one embodiment, the stimulus is at least one of a light, a sound, music, a video showing, e.g., the user or an object, a tactile stimulus, and spoken instructions.

In another aspect, embodiments of the present invention relate to a system for determining at least one physical fitness parameter of a user. The system includes a processor, a body motion sensor, and computer executable instructions operative on said processor for: prompting the user to provide physical characteristics data via an interface, providing a stimulus via the interface to prompt the user to perform an exercise protocol, capturing motion data of said user's body with said body motion sensor, and computing at least one physical fitness parameter utilizing said motion data and said physical characteristics data.

In one embodiment, the at least one physical fitness parameter is selected from the group consisting of maximal oxygen uptake and body composition. In one embodiment, the computer executable instructions further comprise instructions for displaying the computed physical fitness parameter to a user. In one embodiment, the exercise protocol comprises periodic body movements involving a significant number of the user's body muscles. In one embodiment, the body motion data are selected from the group consisting of the amplitude of the motion of the user's body, the speed of the motion of the user's body, the number of repetitions of the motion of the user's body, and the relation between motion features during different parts of the protocol exercise. In one embodiment, the physical characteristics data are selected from the group consisting of the user's body weight, the user's body height, the user's body fat percentage, the user's age, and the user's body mass index.

In one embodiment, the system is a self-contained unit. In one embodiment, computing at least one physical fitness parameter comprises a waveform analysis of the body motion data. In one embodiment, the stimulus is at least one of a light, a sound, music, an image, a video showing, e.g., the user or an object, a tactile stimulus, and spoken instructions. In one embodiment, computing at least one physical fitness parameter includes at least one of a regression analysis and a statistical learning analysis of the body motion data.

In still another aspect, embodiments of the present invention relate to a computer readable medium containing computer-executable instructions for performing a method for determining at least one physical fitness parameter of a user with a computing unit, the method including receiving physical characteristics data concerning the user at the computing unit, providing a stimulus to prompt the user to perform an exercise protocol, receiving data describing the motion of the user's body during the performance of the exercise protocol at the computing unit, and computing at least one physical fitness parameter utilizing said body motion data and said physical characteristics data.

In one embodiment, the at least one physical fitness parameter is selected from the group consisting of maximal oxygen uptake and body composition. In one embodiment, the exercise protocol comprises periodic body movements involving a significant number of the user's body muscles. In one embodiment, the body motion data are selected from the group consisting of the amplitude of the motion of the user's body, the speed of the motion of the user's body, the number of repetitions of the motion of the user's body, and the relation between motion features during different parts of the protocol exercise. In one embodiment, the physical characteristics data are selected from the group consisting of the user's body weight, the user's body height, the user's body fat percentage, the user's age, and the user's body mass index.

These and other features and advantages, which characterize the present non-limiting embodiments, will be apparent from a reading of the following detailed description and a review of the associated drawings. It is to be understood that both the foregoing general description and the following detailed description are explanatory only and are not restrictive of the non-limiting embodiments as claimed.

BRIEF DESCRIPTION OF DRAWINGS

Non-limiting and non-exhaustive embodiments are described with reference to the following Figures in which.

In the drawings, like reference characters generally refer to corresponding parts throughout the different views. The drawings are not necessarily to scale, emphasis instead being placed on the principles and concepts of operation.

DETAILED DESCRIPTION

Various embodiments are described more fully below with reference to the accompanying drawings, which form a part hereof, and which show specific exemplary embodiments. However, embodiments may be implemented in many different forms and should not be construed as limited to the embodiments set forth herein; rather, these embodiments are provided so that this disclosure will be thorough and complete, and will fully convey the scope of the embodiments to those skilled in the art. Embodiments may be practiced as methods, systems or devices. Accordingly, embodiments may take the form of a hardware implementation, an entirely software implementation or an implementation combining software and hardware aspects. The following detailed description is, therefore, not to be taken in a limiting sense.

Reference in the specification to "one embodiment" or to "an embodiment" means that a particular feature, structure, or characteristic described in connection with the embodiments is included in at least one embodiment of the invention. The appearances of the phrase "in one embodiment" in various places in the specification are not necessarily all referring to the same embodiment.

Some portions of the description that follow are presented in terms of symbolic representations of operations on non-transient signals stored within a computer memory. These descriptions and representations are the means used by those skilled in the data processing arts to most effectively convey the substance of their work to others skilled in the art. Such operations typically require physical manipulations of physical quantities. Usually, though not necessarily, these quantities take the form of electrical, magnetic or optical signals capable of being stored, transferred, combined, compared and otherwise manipulated. It is convenient at times, principally for reasons of common usage, to refer to these signals as bits, values, elements, symbols, characters, terms, numbers, or the like. Furthermore, it is also convenient at times, to refer to certain arrangements of steps requiring physical manipulations of physical quantities as modules or code devices, without loss of generality.

However, all of these and similar terms are to be associated with the appropriate physical quantities and are merely convenient labels applied to these quantities. Unless specifically stated otherwise as apparent from the following discussion, it is appreciated that throughout the description, discussions utilizing terms such as "processing" or "computing" or "calculating" or "determining" or "displaying" or the like, refer to the action and processes of a computer system, or similar electronic computing device, that manipulates and transforms data represented as physical (electronic) quantities within the computer system memories or registers or other such information storage, transmission or display devices.

Certain aspects of the present invention include process steps and instructions that could be embodied in software, firmware or hardware, and when embodied in software, could be downloaded to reside on and be operated from different platforms used by a variety of operating systems.

The present invention also relates to an apparatus for performing the operations herein. This apparatus may be specially constructed for the required purposes, or it may comprise a general-purpose computer selectively activated or reconfigured by a computer program stored in the computer. Such a computer program may be stored in a computer readable storage medium, such as, but is not limited to, any type of disk including floppy disks, optical disks, CD-ROMs, magnetic-optical disks, read-only memories (ROMs), random access memories (RAMs), EPROMs, EEPROMs, magnetic or optical cards, application specific integrated circuits (ASICs), or any type of media suitable for storing electronic instructions, and each coupled to a computer system bus. Furthermore, the computers referred to in the specification may include a single processor or may be architectures employing multiple processor designs for increased computing capability.

The processes and displays presented herein are not inherently related to any particular computer or other apparatus. Various general-purpose systems may also be used with programs in accordance with the teachings herein, or it may prove convenient to construct more specialized apparatus to perform the required method steps. The required structure for a variety of these systems will appear from the description below. In addition, the present invention is not described with reference to any particular programming language. It will be appreciated that a variety of programming languages may be used to implement the teachings of the present invention as described herein, and any references below to specific languages are provided for disclosure of enablement and best mode of the present invention.

In addition, the language used in the specification has been principally selected for readability and instructional purposes and may not have been selected to delineate or circumscribe the inventive subject matter. Accordingly, the disclosure of the present invention is intended to be illustrative, but not limiting, of the scope of the invention, which is set forth in the claims.

Embodiments of the present invention relate to the indirect assessment of cardio-respiratory fitness using body motion data. These embodiments derive from the observation that specific measurements of body movement (for example, motion amplitude, movement velocity, distance covered during repetitive displacement, etc.) are dependent on the fitness level of the user. Typically a patient with high flexibility and muscle strength, which are elements correlated to cardio-respiratory fitness, would perform movements in a quicker and more repetitive way than a less fit control subject.

Accordingly, embodiments of the present invention prompt a user to execute a set of periodic movements which typically involve a significant number of body muscles (such as squatting up and down, pull-ups, stand-ups, sit-ups, step exercises, push-ups, walking, running, jumping jacks, line hops, almost every kind of aerobic exercise, etc., preferably involving the lower limbs) and capture various data of interest concerning the user's motion, which can in turn be used to estimate the user's cardiovascular function (e.g., $VO_2^{max}$) and other physical fitness parameters. The body motion data can take various forms, such as activity count, accelerometer signals, cadence of motion, etc. Additional prompts can be presented to the user as they exercise (e.g., using a metronome or similar system) to guide the user as to pacing, etc.

There are several benefits from this process. The use of a simple exercise protocol means that anyone can perform the exercise and obtain an estimate of their fitness almost anytime and everywhere without the assistance of a trained professional such as a doctor or a researcher. The user can perform the exercise protocol at a time and place of their choice, thereby avoiding times of stress, fatigue, outside influence, etc. The only device that the user is required to have on their person is a motion sensor, and suitable sensors are often present in general purpose devices that a user may already possess (such as a smartphone, tablet, or laptop) or devices carried specifically for fitness purposes (such as a pedometer, fitness tracker bracelet, etc.).

Figure 1:
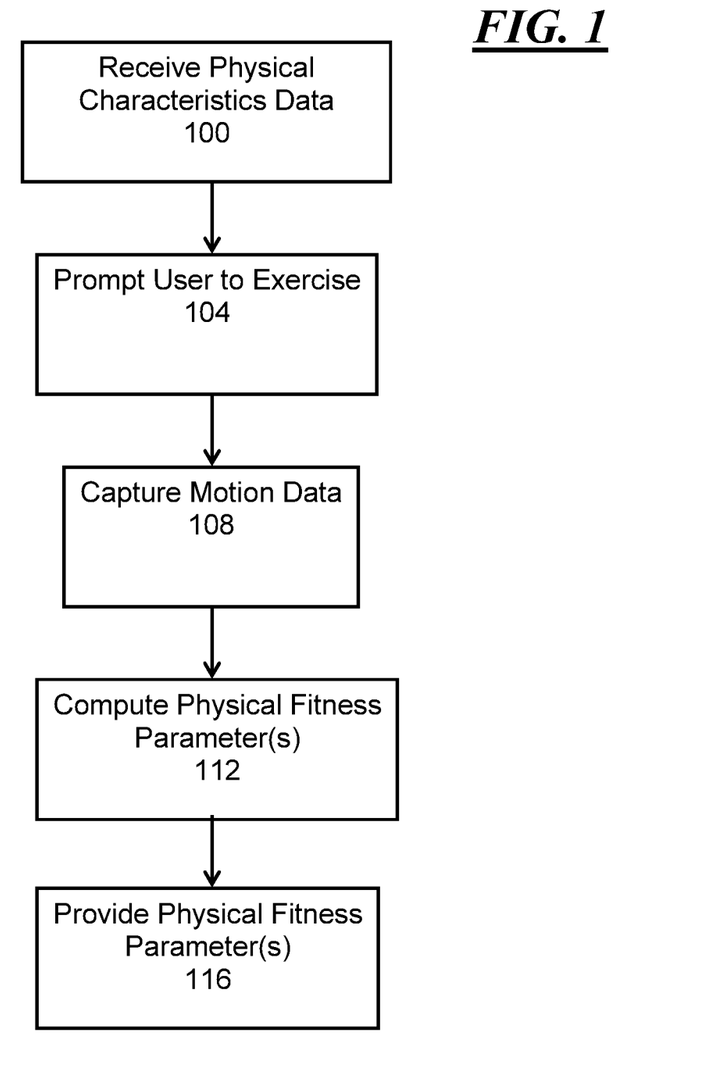
FIG. 1 is a flow diagram illustrating one embodiment of a method for cardio-respiratory fitness assessment in accord with the present invention.

FIG. 1 is a flowchart illustrating one embodiment of a method for cardio-respiratory fitness assessment in accord with the present invention. Initially some data concerning the user's physical characteristics is received at a computing unit (Step 100), although nothing precludes the later entry or subsequent entry or editing in accord with various embodiments of the invention. Physical characteristics data includes, e.g., the user's height or weight, the user's body-mass index (BMI, which itself may be determined from height and weight, or in turn used to determine height or weight).

A stimulus is then provided to prompt the user to perform a specific exercise protocol (Step 104). Suitable stimuli will vary among embodiments, and include flashing or lighting a light, sounding a tone, an image, a video showing, e.g., the user or an object, playing music, issuing spoken instructions (e.g., "Start!" or "Stop!", etc.). In some embodiments the stimulus will coach the user through the performance of the exercise protocol, such as issuing a metronome-like series of sounds to set the rhythm of the protocol or spoken commands (e.g., "Sit!", "Stand!", "Sit!", "Stop!").

The exercise protocol may be selected by the user or automatically selected for the user, and the exercise protocol will typically comprise one or more sets of periodic body movements involving a significant number of the user's body muscles. Typical exercises suitable for the protocol include squats, pull-ups, stand-ups, sit-ups, step exercises, push-ups, walking, running, jumping jacks, line hops, almost every kind of aerobic exercise, etc., preferably involving the lower limbs. As mentioned above, the frequency of individual repetitions of the exercise may be defined by a prompt produced by a programmable metronome or a similar electronic device; the tempo can be chosen a priori in order to elicit an adequate cardiac load from the user.

The computing unit then captures or receives data describing the motion of the user's body during the performance of the exercise protocol (Step 108). As mentioned above, an accelerometer carried on the user's person may enable the tracking of various aspects of physical performance as the user performs the exercise protocol. Typical items of data that may be collected in accord with the present invention may include the time required to perform a single repetition of the exercise, the velocity of the user's body as it performs the protocol, the acceleration at the start and/or end of each repetition, the distance traveled by the user's body during each repetition, the amplitude of the motion of the user's body, the number of repetitions of the motion of the user's body, the differences among any of the foregoing variables as the user performs multiple repetitions of each exercise, etc.

The physical fitness parameter is then computed by utilizing the received body motion data and the received physical characteristics data (Step 112). The combination of body motion data with body measurements (e.g., body weight, height, body fat percentage, BMI, etc.) enables the indirect determination of the user's $VO_2^{max}$ or another parameter representative of the user's physical fitness, such as body composition. In one embodiment, the computation is accomplished by applying a model to at least some of the body motion data and/or the received physical characteristics data. The model may be predetermined or determined as needed by performing a regression analysis, a statistical learning analysis, or both a regression analysis and a statistical learning analysis, of various pre-collected body motion and physical characteristics data.

In some embodiments, the predictive model is determined in advance and customized in operation using one or more of the received physical characteristics data, body motion data, the type of exercise, etc. The customized model is then applied to the body motion data to compute the physical fitness parameter.

In other embodiments, a plurality of predictive models are predetermined in advance and stored. In operation, one of the models is selected using one or more of the received physical characteristics data, body motion data, the type of exercise, etc. The selected model is then applied to the body motion data to compute the physical fitness parameter.

In still other embodiments, a combination of these techniques is utilized, i.e., such that one of a plurality of predictive models is selected using received physical characteristics data, body motion data, the type of exercise, etc., and the selected model is customized using one or more of the received physical characteristics data, body motion data, the type of exercise, etc. before applying the selected, customized model to the body motion data to compute the physical fitness parameter.

An example of a predictive model developed using a multivariate linear regression applied to body motion data collected from twelve heart patients performing a squat test is:

$$VO_2^{max} \text{ predicted normalized by weight} = \alpha_0 + \alpha_1 \times \text{Activity Count}_{squat} \quad \text{(Eq. 1)}$$

The computed physical fitness parameter may be displayed to another user or operator (e.g., a doctor, a nurse, etc.) directly or indirectly via a display, text message, e-mail, spoken message, etc. (Step 116).

Figure 2:
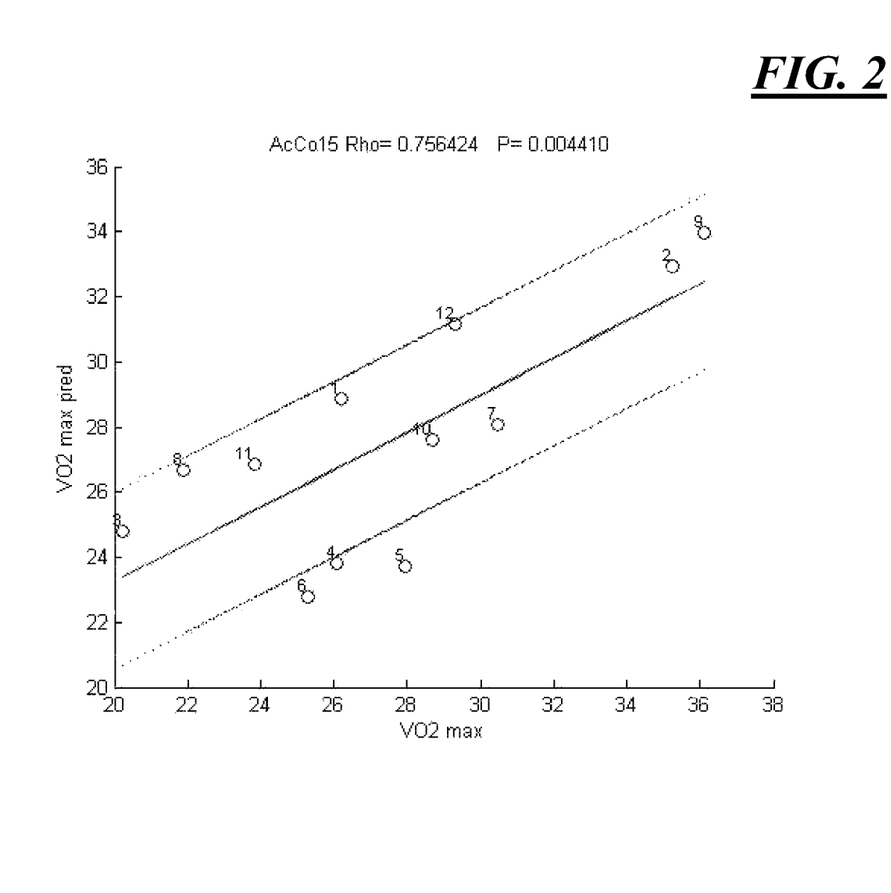
FIG. 2 presents $VO_2^{max}$ as predicted by an embodiment of the present invention compared against $VO_2^{max}$ measured according to a standard cycling protocol.

FIG. 2 presents the $VO_2^{max}$ predicted by the model of Equation 1 using the motion features collected from a 45 second squat test of twelve patients with a metronome set at 80 bpm. The patients had to follow the metronome but were otherwise free to decide the amplitude of the movement and the form for their squat. The $VO_2^{max}$ was measured according to a standard cycling protocol. As is apparent from FIG. 2, the twelve patients cluster into three groups, presumably according to their level of fitness, and the predicted values are substantially similar to the measured values.

Each cluster of data may be analyzed using, e.g., regression analysis, statistical learning analysis, etc. to distill parameters ($\alpha_0$, $\alpha_1$) associated with ranges of physical characteristics data that may be utilized in connection with the model of Equation 1 or a similar model to be applied in various embodiments of the present invention to provide a computed physical fitness parameter using the body motion data and the physical characteristics data of the user under consideration as discussed above.

The data obtained have a correlation coefficient ($\rho$)≈0.76 with a statistical significance (P)≈0.044, a determination coefficient ($R_2$)≈0.58, and a root mean square error $$(RMSE) \approx 3 \frac{\text{ml}}{\text{min} * \text{kg}}.$$

Another example of a predictive model developed using a multivariable linear regression applied to body motion data collected from twelve heart patients performing a squat test is:

$$VO_2^{max} \text{ predicted} = \alpha_0 + \alpha_1 \times \text{weight} + \alpha_2 \times \text{Activity Count}_{squat} \quad \text{(Eq. 2)}$$

Figure 3:
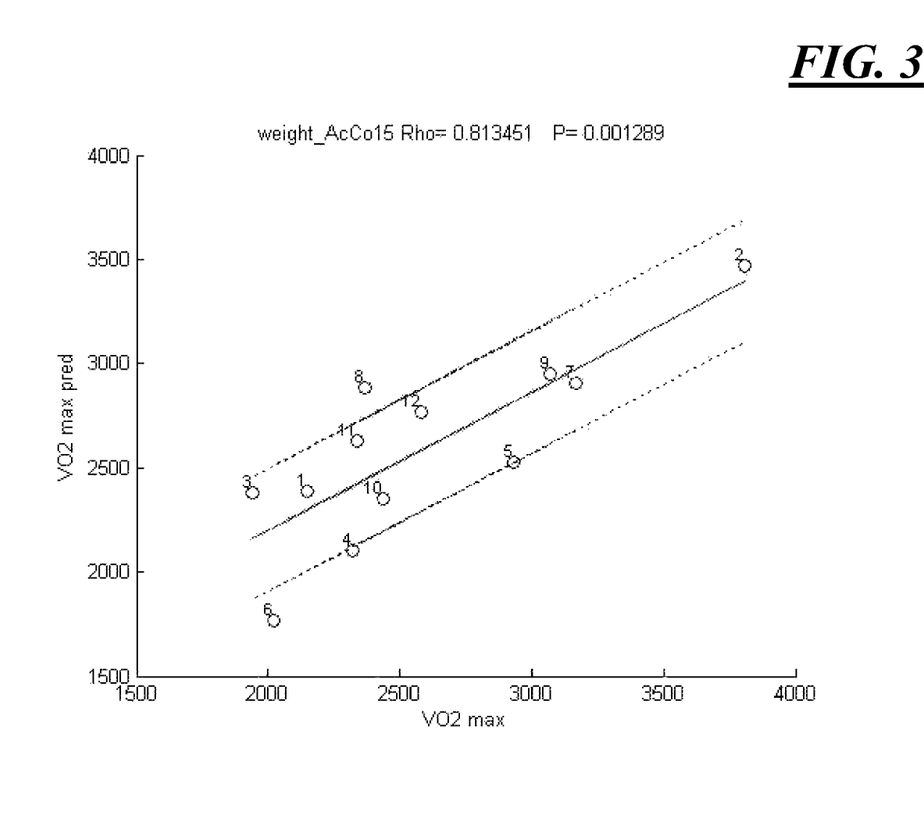
FIG. 3 presents $VO_2^{max}$ as predicted by an embodiment of the present invention accounting for body weight compared against $VO_2^{max}$ measured according to a standard cycling protocol.

FIG. 3 presents the $VO_2^{max}$ predicted by the model of Equation 2 using the motion features collected from a 45 second squat test of twelve patients with a metronome set at 80 bpm. The patients had to follow the metronome but were otherwise free to decide the amplitude of the movement and the form for their squat. The $VO_2^{max}$ was measured according to a standard cycling protocol. As is apparent from FIG. 3, the twelve patients cluster into three groups, presumably according to their level of fitness, and the predicted values are substantially similar to the measured values.

Again, each cluster of data may be analyzed using, e.g., regression analysis, statistical learning analysis, etc. to distill parameters ($\alpha_0$, $\alpha_1$, $\alpha_2$) associated with ranges of physical characteristics data that may be utilized in connection with the model of Equation 2 or a similar model to be applied in various embodiments of the present invention to provide a computed physical fitness parameter using the body motion data and the physical characteristics data of the user under consideration as discussed above.

The data obtained have a correlation coefficient ($\rho$)≈0.81 with a statistical significance (P)≈0.13%, a determination coefficient ($R_2$)≈0.66, and a root mean square error (RMSE) ≈305.54 ml/min.

In another embodiment, a physical fitness parameter is computed by performing a waveform analysis of the body motion data. A user equipped with a motion sensor tracking the user's movement and/or position generates data that is effectively a two or three dimensional time varying waveform. Accordingly, that data may be subjected to various analytical techniques in the time or frequency domain that may be used to determine a physical fitness parameter.

Figure 4:
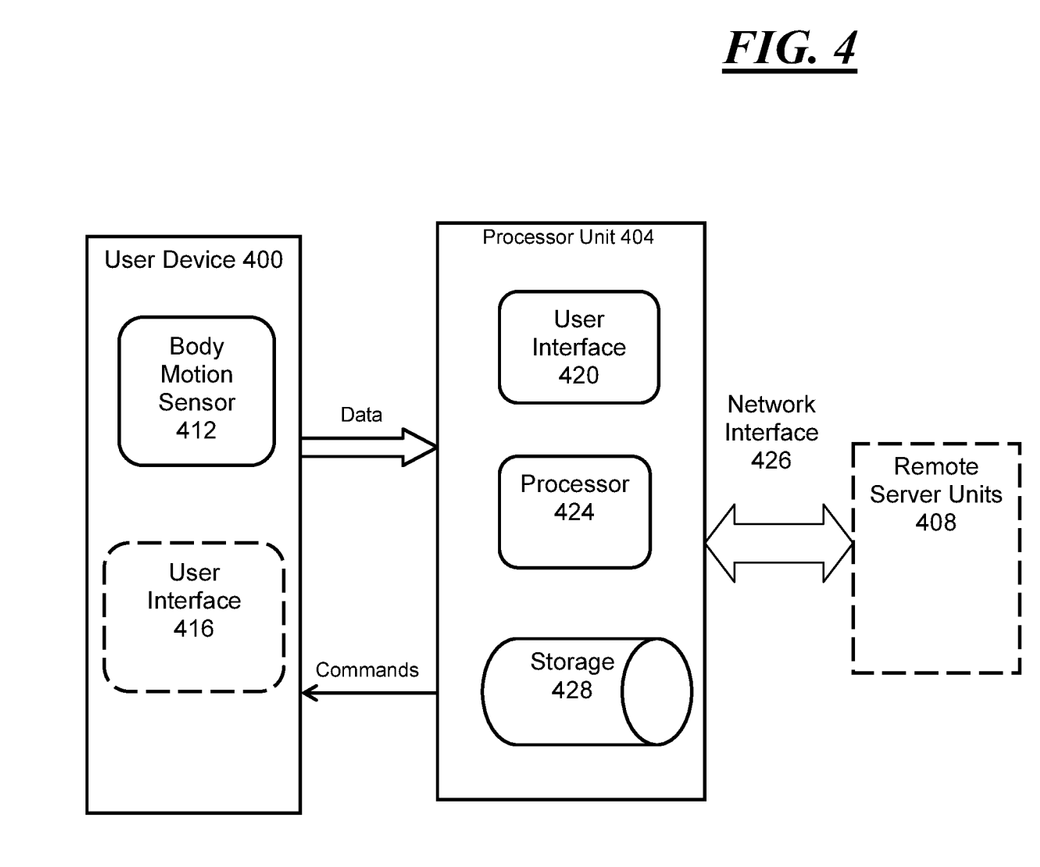
FIG. 4 is a block diagram presenting one embodiment of a system for cardio-respiratory fitness assessment in accord with the present invention.

FIG. 4 is a block diagram illustrating one embodiment of a system for cardio-respiratory fitness assessment including a user device 400 and a processor unit 404.

The user device 400 is primarily responsible for collecting data concerning the user's motion, although it also typically includes an interface for collecting information from and/or providing information to the user. In some embodiments the user device 400 interoperates with a processor unit 404 that is primarily responsible for analyzing the collected data to determine parameters describing the physical fitness of the user.

The user device 400 can take a variety of wearable forms, such as a bracelet, pendant, etc. The processor unit 404 can likewise take a variety of forms, such as a server computer, desktop computer, laptop computer, tablet, phablet, smartphone, etc.

In some embodiments the user device 400 and the processor unit 404 are separate physical devices. For example, the user device 400 may be a bracelet worn by a user while the processor unit 404 may be a desktop computer operated by another user, such as a nurse or a physician. In other embodiments, the functionality of the user device 400 and the processor unit 404 are offered by the same device. In still other embodiments, the processing capabilities of the processor unit 404 may be implemented across the processor unit 404 and one or more additional computing devices, such as remote server units 408. The following discussion assumes the user device 400 and the processor unit 404 to be separate physical devices for convenience, although this should not be construed to be limiting as to the overall scope of the present invention.

As illustrated, the user device 400 includes a body motion sensor 412 and an optional user interface 416. The body motion sensor 412 can include, for example, an accelerometer (single axis or multi-axis) or a location device (such as a GPS receiver, GLONASS receiver, or Galileo receiver). In embodiments where the user device 400 is not carried on the user, then the body motion sensor 412 may be a camera, light detection and ranging device (LIDAR), or other form of sensor used to observe and track the user's motion. The user interface 416 can take many forms, but is typically appropriate to the form of the user device 400. Typical user interfaces 416 include a speech generator, a display (LCD, LED, CRT, E-Ink, etc.), a projector, a keyboard (physical or virtual), a speech recognition system, a touchscreen, etc.

The computing device or processor unit 404 includes a user interface 420, a processor 424, a network interface 426, and a storage unit 428 which acts as a repository for the computer executable instructions that execute on the processor 424 and thereby provide the functionality of the present invention. The interface 420 may, like the interface 416, take a variety of forms that is appropriate to the particular form of the processor unit 404.

In operation, commands are sent from the processor unit 404 to the user device 400. Data is received by the processor unit 404 from the user device 400. Data may be transmitted to and received from a remote server unit 408 by the processor unit 404 via a network interface 426 in embodiments utilizing such remote server units 408.

The user is prompted to provide physical characteristics data (e.g., height, weight, BMI, etc.) via the user interface 416 on the user device 400, although the user may also voluntarily provide such data or provide it using another device, such as processor unit 404. The physical characteristics data may be provided prior to the start of the exercise protocol, after the completion of the exercise protocol, independent of the exercise protocol, etc. The user's physical characteristics data may include the user's body weight, the user's body height, the user's body fat percentage, and the user's body mass index.

A stimulus is provided to prompt the user to perform an exercise protocol via, e.g., the user interface 416 on the user device, the interface 420 on the processor unit 404, etc., as discussed above. The body motion sensor 412 captures the motion data of the user's body, constantly, or coincidentally with the user's motion, with the provision of the prompt, with the start of the measurement or exercise protocol, etc. The exercise protocol may comprise periodic body movements involving a significant number of the user's body muscles, as discussed above.

The body motion data is then received by the processor 424 and processed with the physical characteristics data to compute at least one physical fitness parameter, such as maximal oxygen uptake, body composition, etc., using, e.g., a predictive model as discussed above. The body motion data received at the processor unit 404 may include the amplitude of the motion of the user's body, the speed of the motion of the user's body, the number of repetitions of the motion of the user's body, the relation between motion features during different part of the protocol exercise, etc. The computed physical fitness parameter may be displayed to another user or operator directly or indirectly as discussed above.

In some embodiments, the predictive model is determined in advance and customized in operation using one or more of the received physical characteristics data, body motion data, the type of exercise, etc. The customized model is then applied to the body motion data to compute the physical fitness parameter.

In other embodiments, a plurality of predictive models are predetermined in advance and stored. In operation, one of the models is selected using one or more of the received physical characteristics data, body motion data, the type of exercise, etc. The selected model is then applied to the body motion data to compute the physical fitness parameter.

In still other embodiments, a combination of these techniques is utilized, i.e., such that one of a plurality of predictive models is selected using received physical characteristics data, body motion data, the type of exercise, etc., and the selected model is customized using one or more of the received physical characteristics data, body motion data, the type of exercise, etc. before applying the selected, customized model to the body motion data to compute the physical fitness parameter.

In a related aspect of the invention, a physical fitness parameter is computed by performing a waveform analysis of the body motion data. The physical fitness parameter may also be computed by performing a multivariate linear regression analysis, a statistical learning analysis, or both a regression analysis and a statistical learning analysis, of the body motion data.

Figure 5:
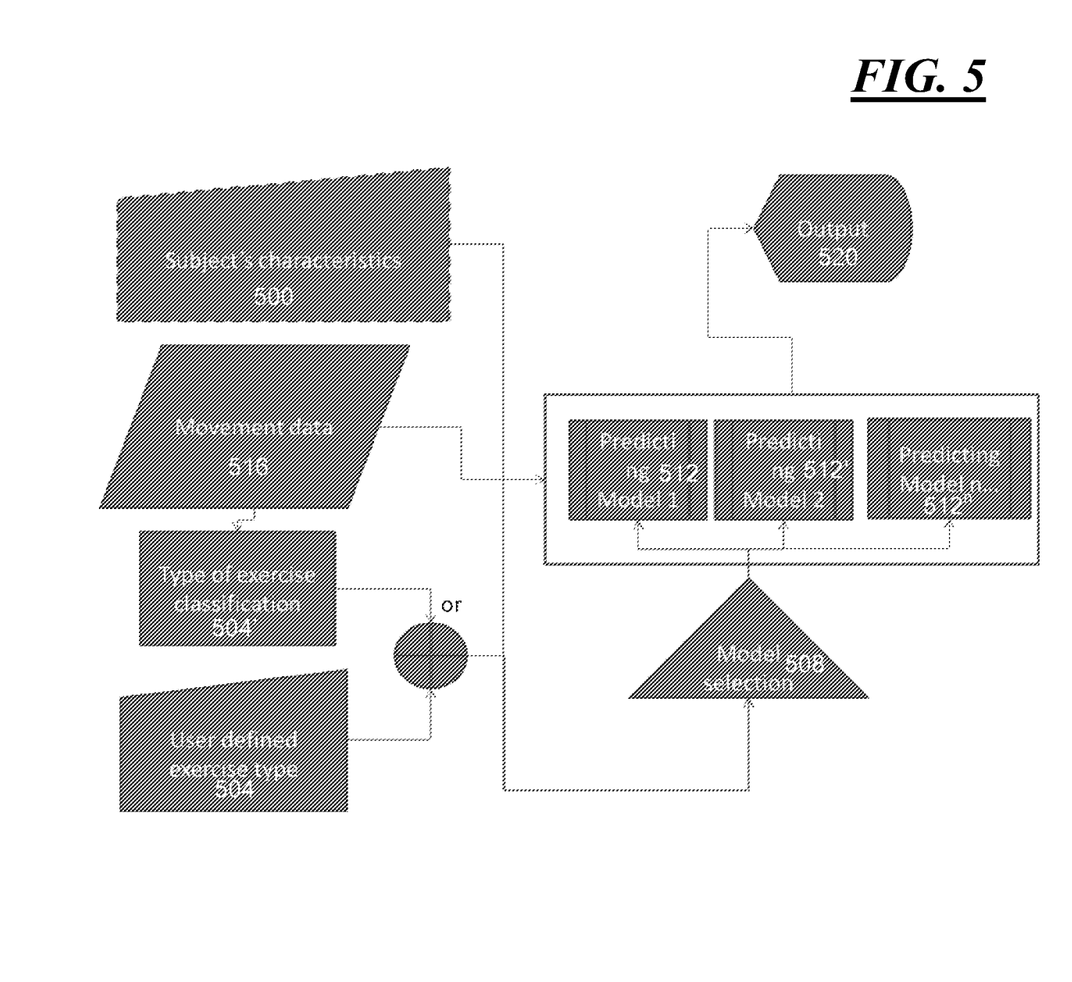
FIG. 5 is a flowchart illustrating the computation of physical fitness parameters in accord with the present invention.

FIG. 5 presents a flowchart depicting the computation of physical fitness parameters in accord with the present invention. Physical characteristics data 500 concerning the user (e.g., height, weight, age, BMI, etc., as discussed above) and the type of exercise 504 being performed by the user are used to select 508 one or more predictive models 512 that are predetermined and/or preloaded as discussed above. The type of exercise may be explicitly specified by the user 504 or it may be inferred 504' from the user's movement data 516. The selected model(s) 512 are then applied to the user's movement data 516 to compute at least one physical fitness parameter, which is then output 520.

In another embodiment of the invention, a computer readable medium contains computer-executable instructions for performing a method for determining at least one physical fitness parameter of a user as discussed above.

Embodiments of the present disclosure, for example, are described above with reference to block diagrams and/or operational illustrations of methods, systems, and computer program products according to embodiments of the present disclosure. The functions/acts noted in the blocks may occur out of the order as shown in any flowchart. For example, two blocks shown in succession may in fact be executed substantially concurrent or the blocks may sometimes be executed in the reverse order, depending upon the functionality/acts involved. Additionally, not all of the blocks shown in any flowchart need to be performed and/or executed. For example, if a given flowchart has five blocks containing functions/acts, it may be the case that only three of the five blocks are performed and/or executed. In this example, any of the three of the five blocks may be performed and/or executed.

The description and illustration of one or more embodiments provided in this application are not intended to limit or restrict the scope of the present disclosure as claimed in any way. The embodiments, examples, and details provided in this application are considered sufficient to convey possession and enable others to make and use the best mode of the claimed embodiments. The claimed embodiments should not be construed as being limited to any embodiment, example, or detail provided in this application. Regardless of whether shown and described in combination or separately, the various features (both structural and methodological) are intended to be selectively included or omitted to produce an embodiment with a particular set of features. Having been provided with the description and illustration of the present application, one skilled in the art may envision variations, modifications, and alternate embodiments falling within the spirit of the broader aspects of the general inventive concept embodied in this application that do not depart from the broader scope of the claimed embodiments.

What is claimed is:

1. A method for determining at least one physical fitness parameter of a user with a computing circuit, the method comprising:
    receiving, by the computing circuit, physical characteristics data concerning the user at the computing circuit;
    accessing, by the computing circuit, a database that includes a plurality of predictive models,
        wherein each predictive model is based on a type of exercise of a plurality of types of exercise,
        wherein each predictive model enables a determination of the at least one physical fitness parameter based on the type of exercise and body motion data;
    selecting a selected type of exercise from the plurality of types of exercise,
        wherein the selected type of exercise corresponds to a selected exercise protocol;
    selecting, by the computing circuit, a selected predictive model based on the selected type of exercise;
    providing, by the computing circuit, a stimulus to prompt the user to perform the exercise protocol corresponding to the selected type of exercise;
    receiving, from a body motion sensor, body motion data of the user during the performance of the exercise protocol;
    computing, in real time, by the computing circuit, at least one physical fitness parameter utilizing the selected predictive model, based on the body motion data and the physical characteristics data, wherein the at least one physical fitness parameter is selected from the group consisting of maximal oxygen uptake and body composition; and
    displaying, in real time, on a display device, the at least one physical fitness parameter to the user.

2. The method of claim 1, wherein the plurality of types of exercise comprises two or more of a squatting motion, a stand-up motion, a sit-ups motion, a push-ups motion, a jumping jacks motion, or a line-hops motion.

3. The method of claim 1, wherein the body motion data are selected from the group consisting of the amplitude of the motion of the user's body, the speed of the motion of the user's body, the number of repetitions of the motion of the user's body, and the relation between motion features during different parts of the exercise protocol.

4. The method of claim 1, wherein the physical characteristics data are selected from the group consisting of the user's body weight, the user's body height, the user's body fat percentage, the user's age, and the user's body mass index.

5. The method of claim 1, wherein computing the at least one physical fitness parameter comprises a waveform analysis of the body motion data.

6. The method of claim 1, wherein the stimulus is at least one of a light, a sound, music, an image, a video, a tactile stimulus, and spoken instructions.

7. A system for determining at least one physical fitness parameter of a user, the system comprising:
    a processor circuit;
    a body motion sensor; and
    non-transitory computer executable instructions that cause the processor circuit to:
        receive physical characteristics data related to the user;
        access a database that includes a plurality of predictive models,
            wherein each predictive model is based on a type of exercise of a plurality of types of exercise,
            wherein each predictive model enables a determination of the at least one physical fitness parameter based on the type of exercise and body motion data,
            wherein at least two of the predictive models are different from each other;
        identify a selected type of exercise from the plurality of types of exercise,
            wherein the selected type of exercise corresponds to a selected exercise protocol;
        select a selected predictive model based on the selected type of exercise;
        provide a stimulus to prompt the user to perform the selected exercise protocol;

capture body motion data from the body motion sensor while the user is performing the selected exercise protocol;

compute in real time, the at least one physical fitness parameter utilizing the selected predictive model, based on the body motion data and the physical characteristics data, wherein the at least one physical fitness parameter is selected from the group consisting of maximal oxygen uptake and body composition; and display in real time, the at least one physical fitness parameter to the user.

8. The system of claim 7, wherein the plurality of types of exercise comprises at least two of: a squatting motion, a stand-up motion, a sit-ups motion, a push-ups motion, a jumping jacks motion, or a line-hops motion.

9. The system of claim 7, wherein the body motion data are selected from the group consisting of the amplitude of the motion of the user's body, the speed of the motion of the user's body, the number of repetitions of the motion of the user's body, and the relation between motion features during different parts of the exercise protocol.

10. The system of claim 7, wherein the physical characteristics data are selected from the group consisting of the user's body weight, the user's body height, the user's body fat percentage, the user's age, and the user's body mass index.

11. The system of claim 7, wherein the system is a self-contained unit.

12. The system of claim 7, wherein computing the at least one physical fitness parameter comprises a waveform analysis of the body motion data.

13. The system of claim 7, wherein the stimulus is at least one of a light, a sound, music, a video, an image, a tactile stimulus, and spoken instructions.

14. A non-transitory computer-readable medium containing computer-executable instructions that, when executed by a processing system, causes the processing system to:

receive physical characteristics data concerning the user;

access a database that includes a plurality of predictive models, wherein each predictive model is based on a type of exercise of a plurality of types of exercise, wherein each predictive model enables a determination of the at least one physical fitness parameter based on the type of exercise and body motion data;

identify a selected type of exercise from the plurality of types of exercise, wherein the selected type of exercise corresponds to a selected exercise protocol;

select a selected predictive model based on the selected type of exercise;

provide a stimulus to prompt the user to perform the selected exercise protocol;

receive, from a body motion sensor, body motion data of the user's body during the performance of the selected exercise protocol;

compute at least one physical fitness parameter utilizing the selected predictive model, based on the body motion data and the physical characteristics data; and display the at least one physical fitness parameter to the user.

15. The medium of claim 14, wherein the plurality of types of exercise comprises at least two of: a squatting motion, a stand-up motion, a sit-ups motion, a push-ups motion, a jumping jacks motion, or a line-hops motion.

16. The medium of claim 14, wherein the selected exercise protocol comprises periodic body movements involving a significant number of the user's body muscles.

17. The medium of claim 14, wherein the body motion data are selected from the group consisting of the amplitude of the motion of the user's body, the speed of the motion of the user's body, the number of repetitions of the motion of the user's body, and the relation between motion features during different parts of the exercise protocol.

18. The medium of claim 14, wherein the physical characteristics data are selected from the group consisting of the user's body weight, the user's body height, the user's body fat percentage, the user's age, and the user's body mass index.

19. The medium of claim 14, wherein computing the at least one physical fitness parameter comprises a waveform analysis of the body motion data.

20. The medium of claim 14, wherein the selected predictive model comprises at least one of: a regression analysis, a statistical learning analysis, and both a regression analysis and a statistical learning analysis, of the body motion data.

21. The medium of claim 15, wherein the instructions cause the processing system to identify the selected type of exercise by receiving an indication of the selected type of exercise by the user.

22. The method of claim 1, wherein the selecting of the selected type of exercise is controlled by the user.

* * * * *